(12) United States Patent
Funk

(10) Patent No.: US 9,784,696 B2
(45) Date of Patent: *Oct. 10, 2017

(54) METHOD FOR CONTROLLING X-RAY EXPOSURE

(71) Applicant: Triple Ring Technologies, Inc., Newark, CA (US)

(72) Inventor: Tobias Funk, Martinez, CA (US)

(73) Assignee: Triple Ring Technologies, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/333,113

(22) Filed: Oct. 24, 2016

(65) Prior Publication Data

US 2017/0045464 A1   Feb. 16, 2017

Related U.S. Application Data

(63) Continuation of application No. 14/943,011, filed on Nov. 16, 2015, now Pat. No. 9,476,845, which is a continuation of application No. 14/714,083, filed on May 15, 2015, now Pat. No. 9,188,549, which is a continuation of application No. 13/896,208, filed on May 16, 2013, now Pat. No. 9,036,770.

(60) Provisional application No. 61/774,289, filed on Mar. 7, 2013.

(51) Int. Cl.
    *A61B 6/00*    (2006.01)
    *G01N 23/04*   (2006.01)
    *A61B 6/14*    (2006.01)
    *G06T 11/00*   (2006.01)

(52) U.S. Cl.
    CPC ............. *G01N 23/046* (2013.01); *A61B 6/14* (2013.01); *G06T 11/005* (2013.01); *G01N 2223/419* (2013.01); *G06T 2210/41* (2013.01)

(58) Field of Classification Search
    CPC ........ G01N 23/046; A61B 6/14; G06T 11/005; G06T 2210/419
    USPC .......................................... 378/4–20, 62, 108
    See application file for complete search history.

(56) References Cited

U.S. PATENT DOCUMENTS

| | | | | |
|---|---|---|---|---|
| 5,867,555 A | * | 2/1999 | Popescu ................. | A61B 6/032 378/16 |
| 9,036,770 B2 | * | 5/2015 | Funk .................... | G01N 23/046 378/16 |

(Continued)

*Primary Examiner* — Courtney Thomas
(74) *Attorney, Agent, or Firm* — Joseph T. Lin; Sabrina N. David

(57) ABSTRACT

The present invention pertains to a system and method for X-ray imaging wherein a targeted fluence at the detector for projection images can be achieved at a plurality of projection angles around the imaging subject by control of exposure times implemented during image acquisition. Exposure time for a second projection image may be determined by the fluence in a first projection image, and in a third projection image by the fluence in a second projection image, where projection images are acquired within two degrees of one another. An acquisition parameter calculation can be configured to calculate acquisition parameters, such as said exposure times, to achieve the targeted fluence in projection images and can be coupled to a rotation controller that implements the acquisition parameters by controlling a relative angle between the imaging subject and X-ray image acquisition device.

12 Claims, 5 Drawing Sheets

(56) References Cited

U.S. PATENT DOCUMENTS 9,188,549 B2 * 11/2015 Funk ................ G01N 23/046
9,476,845 B2 * 10/2016 Funk ................ G01N 23/046

* cited by examiner

METHOD FOR CONTROLLING X-RAY EXPOSURE

RELATED U.S. APPLICATION

This application is a continuation application claiming priority from the co-pending U.S. non-provisional patent application, Ser. No. 14/943,011, entitled "METHOD AND APPARATUS FOR CONTROLLING FLUENCE IN COMPUTED X-RAY IMAGING," with filing date Nov. 16, 2015. U.S. non-provisional patent application, Ser. No. 14/943,011 claims priority to U.S. non-provisional patent application, Ser. No. 14/714,083, entitled "METHOD AND APPARATUS FOR CONTROLLING DOSE IN COMPUTED X-RAY IMAGING," with filing date May 15, 2015. U.S. non-provisional patent application, Ser. No. 14/714,083 claims priority to U.S. non-provisional patent application, Ser. No. 13/896,208, entitled "SYSTEM AND METHOD FOR SAVING TIME AND DOSE IN COMPUTED TOMOGRAPHY," with filing date May 16, 2013. U.S. non-provisional patent application, Ser. No. 13/896,208 claims priority to U.S. provisional patent application, Ser. No. 61/774,289, entitled "System and Method for Improved Contrast-to-Noise in Computed Tomography," with filing date Mar. 7, 2013, all of which are hereby incorporated by reference in their entirety.

FIELD OF THE INVENTION

The present invention pertains to systems and methods for computed tomography. The present invention also pertains to systems and methods for computed tomography in industrial metrology and dental applications.

BACKGROUND

Computed tomography (CT) is an X-ray imaging modality that providing the ability to non-invasively gain information about three-dimensional structure within an object. While computed tomography has been pervasive in medical, diagnostic, and intraoperative applications since its development in 1972, it has also been tailored to industrial applications mostly since the 1990's. Industrial metrology systems are described, for example, in U.S. Pat. Nos. 5,027,378 and 4,422,177.

Industrial computed tomography systems, e.g., such as coordinate measuring machines (CMM), can allow objects and work pieces, which may have external and internal structure made of metal, plastics, composites, and other materials, to be investigated without disassembly or destruction. Non-destructive measurement or investigation can be particularly useful in a final stage of industrial manufacturing, where a work piece may require validation of precise dimensions and internal construction. This capability can also be useful for later stage analysis, such as failure prediction or analysis.

To allow precise measurements of a work piece or detection of fine defects, such as cracks, vacancies, or similar features, industrial CT systems may utilize microfocus X-ray sources for their ability to provide micron-level resolution. Microfocus X-ray tubes can be relatively limited in operating power relative to sources having larger focal spots due to the enhanced localization of the thermal load in the anode. Potentially high densities or large sizes of work pieces in conjunction with relatively lower X-ray tube power can cause scan times in industrial metrology to be significantly longer than for medical CT scans. Overly long scan times can limit throughput of a manufacturing operation.

Computed tomography systems have also been tailored for dental imaging applications in recent years. Dental computed tomography images can provide information including the structure and density of teeth and jaw bones and the positioning of nerves. This information can be useful for various types of surgical planning as well as improving the ability to complete a pre-surgical assessment of whether a patient is a good candidate for dental implants.

The utility of computed tomography images in metrology, dental, and other applications can be dependent not only on image resolution but also on image quality aspects such as the contrast-to-noise ratio (CNR) of the image, presence of artifacts that obscure image details, or other aspects that affect the ability to resolve true internal features of the imaging subject. These aspects of image quality can be determined by a variety of factors, including the X-ray tube power and total scan time. What is needed is a system and method of providing high image quality within scan time and tube power constraints of a CT application.

SUMMARY

The present invention pertains to a system and method for X-ray imaging wherein a targeted detector fluence for projection images can be achieved at a plurality of projection angles around the imaging subject by control of exposure times implemented during image acquisition. The plurality of projection angles may comprise at least 200 unique relative angles between the X-ray image acquisition device and an axis of the imaging subject spanning at least 180 degrees around the subject. Targeted exposure times can be determined by simulating expected detector fluence for projection images or by acquiring a preliminary image data set with uniform exposure times and less than 50% of the X-ray source power to be used for image acquisition or by the full X-ray source power to be used for image acquisition. Alternatively, exposure time for a second projection image may be determined by the detector fluence in a first projection image, and in a third projection image by the detector fluence in a second projection image, where projection images are acquired within two degrees of one another. The subject or image acquisition device can be continuously rotated during image acquisition, such as by determination and implementation of a rotational velocity sequence, or images can be acquired with the subject and imaging device being stationary at each projection angle. An X-ray image can be reconstructed from acquired image data.

An acquisition parameter calculation can be configured to calculate acquisition parameters, such as said exposure times, to achieve the targeted detector fluence in projection images and can be coupled to a rotation controller that implements the acquisition parameters by controlling a relative angle between the imaging subject and X-ray image acquisition device, such as by controlled rotation of the imaging subject stage or the image acquisition device. A feedback loop may be provided between the rotation controller and the element that it controls.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Figure 1:
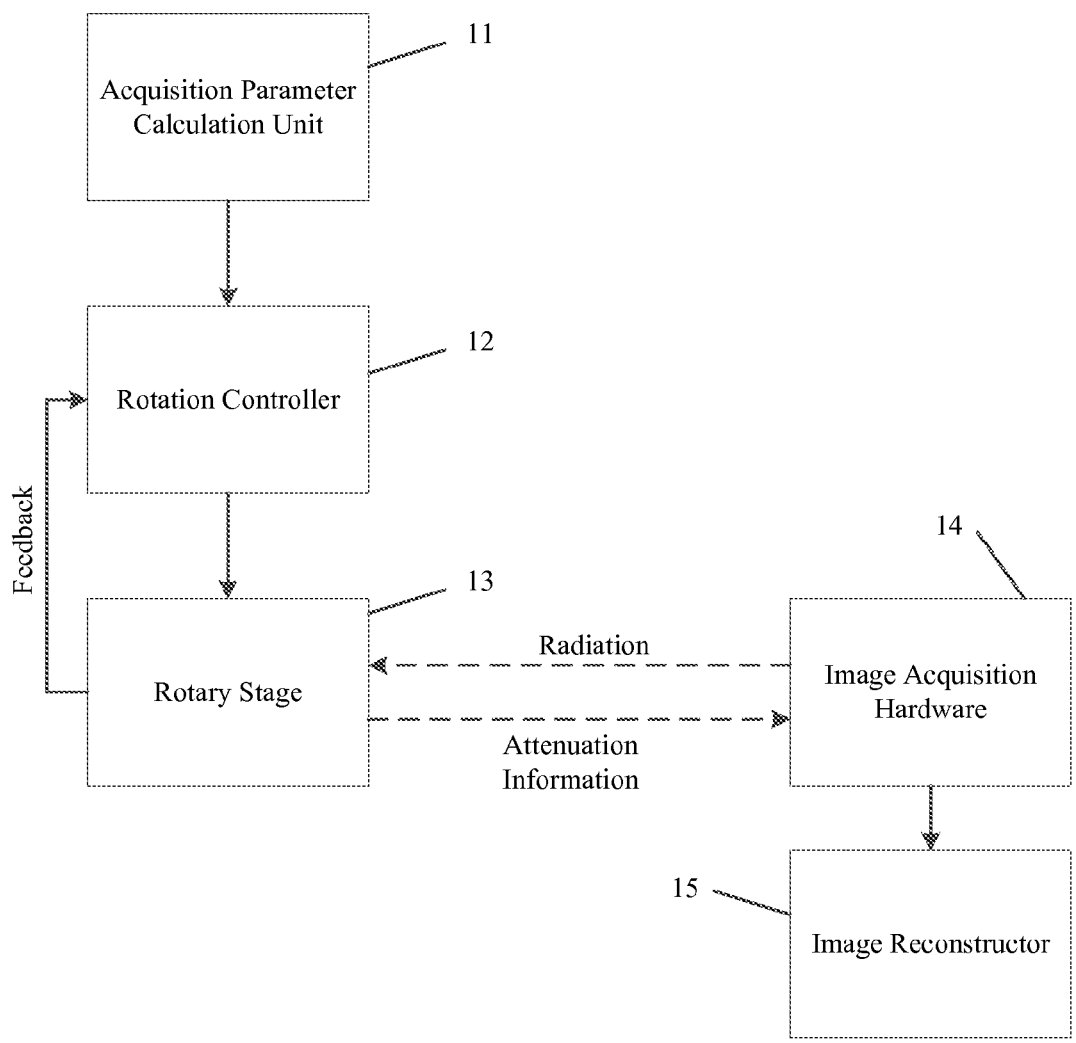
FIG. 1 is a diagram representing one system of an embodiment of the present invention wherein an object can be imaged on a rotary stage, rotation of the rotary stage being controlled according to measured or expected attenuation characteristics of the object.

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

The image quality of a computed tomography image can be related to the projection image in a set having highest noise level across all projections in the set. High noise in a single or few projections in a CT data set can result in streaking artifacts or other undesirable effects in reconstructed images, even if many other projections in the data set have relatively low noise. The noise level of each projection may be related to the amount of photon attenuation occurring through the object at that projection angle; noise can scale as $\sim 1/\sqrt{N}$, N being the number of photons per unit of detector area, e.g. the detector fluence. X-ray photon flux along a given path through an object may be predicted by the equation:

$$I = I_0 e^{-\int \mu(x)x\,dx}$$

where I is the X-ray photon flux, if the attenuation coefficients ($\mu$) at positions (x) through the object and the X-ray photon flux of the incident x-ray beam ($I_0$) are predetermined. Fluence can be determined by the integral or sum of detector flux in a given area over the exposure time. Projections of an object in which the paths through the object are particularly thick, comprise material with high attenuation coefficients, or that have some combination of these properties, may exhibit more noise relative to projections in which paths are thinner or comprise materials with lower attenuation coefficients.

In existing implementations of computed tomography, acquisition hardware or, in some cases, the object being imaged, is rotated at a constant angular speed during imaging. In these systems, projections can be exposed with more or less photons depending on their attenuation characteristics by x-ray tube current modulation. However, tube current can only be modulated up to a predetermined maximum current without exceeding performance limits of the tube. X-ray tube current modulation can therefore be tailored to reducing radiation dose, e.g., to decreasing exposure in a few predetermined projections, but not easily to improving the image quality of a final image. In embodiments of the present invention exposure of projections can be modulated based on attenuation characteristics in a manner to decrease noise in highly attenuating regions and to improve the quality of the final reconstructed image.

In embodiments of the present invention, detector fluence at various projection angles may be modulated by controlling the exposure time of each projection angle or the number of exposures taken at that projection angle. However, these embodiments do not necessarily require increasing the total scan time to accommodate increased exposure times at relatively attenuating projections; instead, the increased time at relatively attenuating projection angles can be compensated by implementing decreased exposure times or fewer acquisitions at relatively transparent projection angles. Decreasing the exposure time at relatively transparent projection angles in these embodiments may not affect the image quality, e.g., introduce or enhance artifacts, of the final reconstructed image as long as the exposure times are not decreased below a point at which noise performance becomes worse than in the relatively opaque regions. Decreasing exposure times for relatively transparent projection angles may have additional benefits such as reduced occurrences of detector saturation.

FIG. 1 is a diagram representing one system of an embodiment of the present invention wherein an object can be imaged on a rotary stage, rotation of the rotary stage being controlled according to measured or expected attenuation characteristics of the object. Methods of determining rotation controls according to measured or expected attenuation characteristics are discussed in more detail with respect to FIG. 3 and FIG. 5 below. Image acquisition hardware 14 can be utilized to acquire projection images of an object mounted on a rotary stage 13. Rotary stage 13 can be any type of rotary stage including but not limited to a mechanical-, hydraulic-, or pneumatic-bearing rotary stage or any other type of rotatable platform. Rotation of stage 13 during image acquisition can be controlled by a rotation controller 12, including but not limited to a DC motor, stepper motor, servomotor, worm drive, encoder, actuator, or any similar controller or combinations thereof Feedback between rotary stage 13 and rotation controller 12 may optionally be included to validate positioning of rotary stage 13. For example, rotary stage 13 may be equipped with an active sensor to independently measure the acquisition angle. A feedback loop between the active sensor and rotation controller 12 may validate or correct positioning of the rotary stage.

Inputs or instructions for rotation controller 12 can be determined by an acquisition parameter calculation unit 11. Acquisition parameter calculation unit 11 can be implemented in any type of computational engine, including but not limited to a microprocessor, microcontroller, desktop computer, single- or multi-core processor, calculation engine embedded in another device, or any other computational engine or combinations thereof. An image reconstructor 15 receiving data from image acquisition hardware 14 can also be implemented in a computational engine, including but not limited to those listed above.

Figure 2:
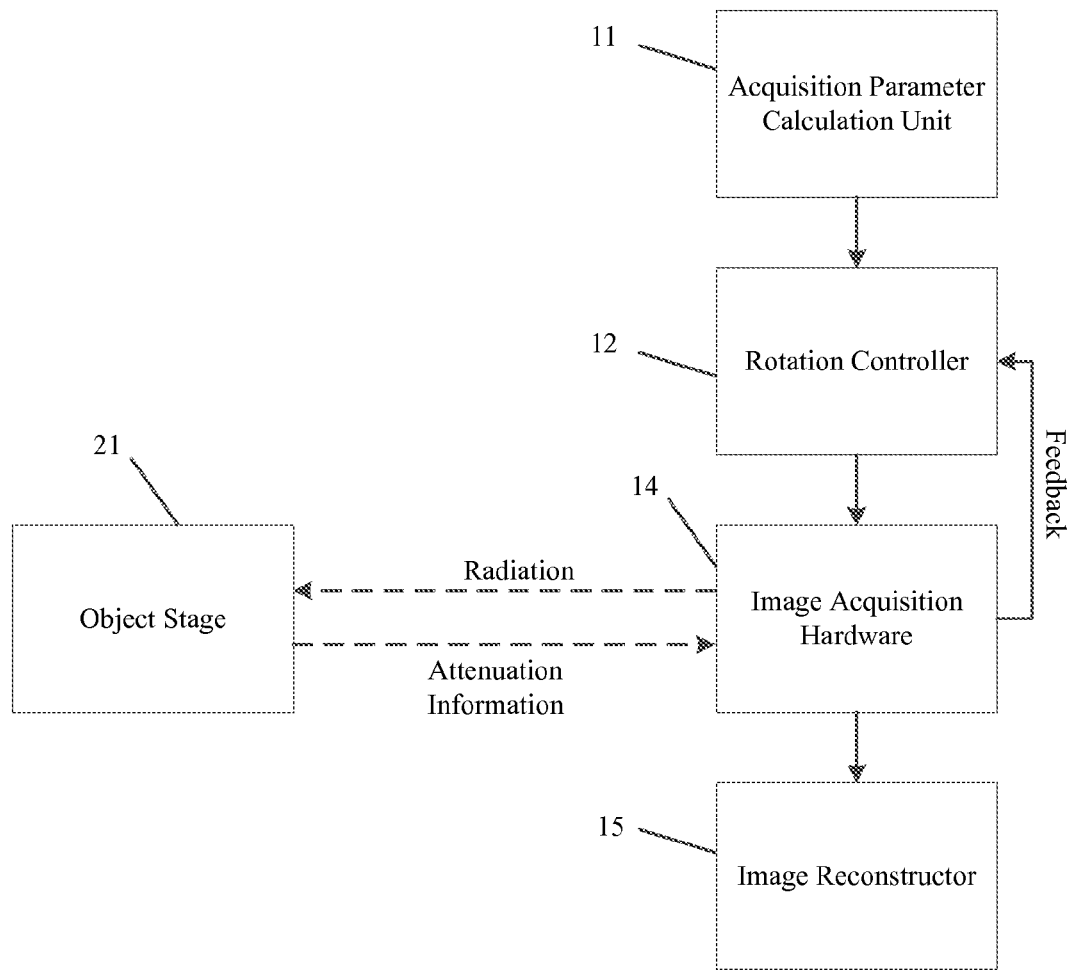
FIG. 2 is a diagram representing a system of an embodiment of the present invention wherein image acquisition hardware can be rotated around an object being imaged, rotation of the rotary stage being controlled according to measured or expected attenuation characteristics of the object.

FIG. 2 is a diagram representing a system of an embodiment of the present invention wherein image acquisition hardware can be rotated around an object being imaged, rotation of the rotary stage being controlled according to measured or expected attenuation characteristics of the object. Similarly to the embodiment of FIG. 1, the embodiment of FIG. 2 may comprise an acquisition parameter calculation unit 11, rotation controller 12, image acquisition hardware 14, and image reconstructor 15. However, a stage 21 wherein an imaging subject is positioned may be stationary, and rotation controller 12 may instead be coupled to image acquisition hardware 14. Stage 21 may be comprise a platform, cage, or other type of support structure, e.g., configured to support a work piece other object. Stage 21 may alternatively comprise a dental bite structure, e.g., configured for precise positioning and to control motion of a human head, chair, bed, or other structure configured for a human imaging subject. Feedback may optionally be provided for validation of the positioning of image acquisition hardware 14.

In the embodiments of FIG. 1 and FIG. 2, image acquisition hardware 14 can comprise a radiation source or sources, including but not limited to x-ray sources comprising reflection or transmission targets, microfocus x-ray sources, rotating anode sources, or any other type of x-ray beam source. In one embodiment of the present invention, the maximum tube current of the source may be between 0.1 mA and 100 mA. The maximum tube current may also be between 0.5 mA and 10 mA, 1 mA and 7 mA, 1 mA and 3 mA, 3 mA and 1 A, or 1 A and 5 A, inclusive, or any integer or non-integer number of milliamps or amps within the enumerated ranges.

Image acquisition hardware 14 can also comprise a radiation detector or detector array including but not limited to photon-counting, energy-integrating, energy-resolving, flat panel, or any other type of radiation detector. In one embodiment, the radiation detector can be a flat panel radiation detector having side lengths between 10 cm and 100 cm, inclusive, e.g., such as 20 cm or 41 cm. The flat panel detector may be any type of direct flat panel detector, including but not limited to Li-doped Si or Ge direct flat panel detectors or amorphous Se direct flat panel detectors. The flat panel detector may alternatively be any type of indirect flat panel detector, including but not limited to amorphous Si detectors coupled with scintillating materials.

Image acquisition hardware 14 can further comprise source- or detector-related hardware and electronics, including without limitation mechanical support structures, detector read electronics, signal processors or amplifiers, external power supplies, anti-scatter grids, x-ray beam filters such as bowtie filters, or any other related hardware or electronics. Support structures may be configured to implement a source-to-detector between 20 cm and 160 cm, inclusive.

The source-to-detector distance can, for example, be 20 cm, 40 cm, 60 cm, 80 cm, or any other integer or non-integer number of centimeters within the enumerated range. The source-to-detector distance may be fixed or variable. Rotary stage 13 or stage 21 may be positioned relative to image acquisition hardware 14 to implement an object-to-detector, e.g. distance from the imaging subject to the detector, between 4 cm and 130 cm, inclusive. An object-to-detector distance may be up to 80% of the source-to-detector distance. The position of the stage may be fixed or variable.

In embodiments of the present invention, scans can comprise rotation of the acquisition hardware or rotary stage through any set of projection angles at least sufficient for a complete CT data set, e.g., 180° plus the angle of a cone or fan beam. This set of angles may be between 180° and 360° around the object. This set of angles may further include between 180° and 200°, 200° and 230°, 230° and 270°, or 270° and 320° around the object, inclusive. The number of projections acquired during a scan may vary across application and desired image quality. For example, in industrial metrology applications, work pieces can sometimes be imaged using over 1,000 unique projection angles. However, embodiments of the present invention may also acquire between 100 and 500 projections, 500 and 900 projection, or 900 and 1500 projections, inclusive, or any other number of projections within or between the enumerated ranges.

Scans may also comprise linear motion between image acquisition hardware and the imaging subject. For example, rotary stage 13 or stage 21 of the embodiments of FIG. 1 and FIG. 2, respectively, can be moved along a central axis between the x-ray source and detector, e.g., to complete a helical scan. Alternatively, the x-ray source and detector can be moved along an axis of the imaging subject. However, embodiments of the present invention may also be implemented without such linear motion, and a complete imaging subject, or a region of interest within the imaging subject, can be captured by a non-helical scan.

Figure 3:
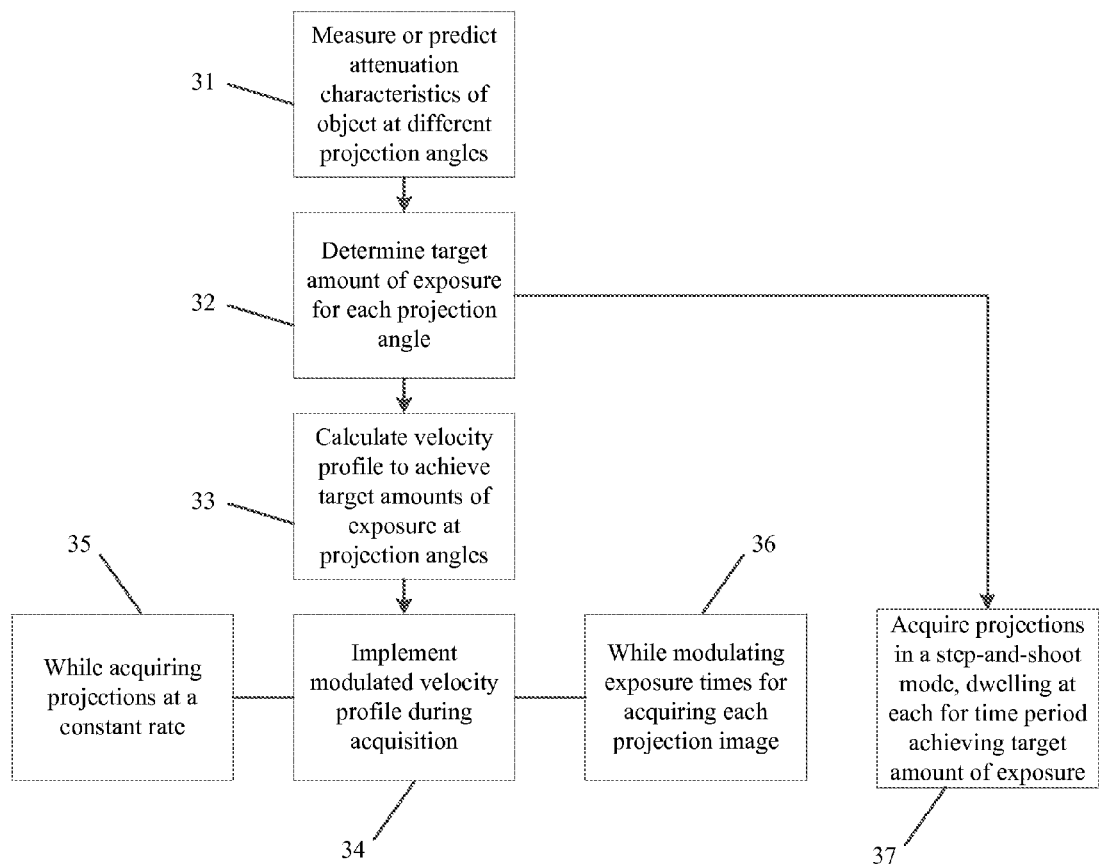
FIG. 3 is a flow diagram showing a number of the embodiments described above that comprise measuring or predicting the attenuation characteristics of an object at different projection angles, determining a target amount of exposure for each projection angle, and implementing a pattern of acquisition that achieves these target amounts of exposure

FIG. 3 is a flow diagram showing methods that comprise measuring or predicting the attenuation characteristics of an object at different projection angles, determining a target amount of exposure for each projection angle, and implementing a pattern of acquisition that achieves these target amounts of exposure of embodiments of the present invention. Attenuation characteristics of the object to be imaged from different projection angles can be measured or predicted (S31) in a variety of ways. In one embodiment, the dimensions and material composition that should be exhibited by the work piece may be predicted or predetermined. For example, the goal of coordinate-measurement metrology (CMM) or similar industrial metrology applications can be validation of measurements of work pieces against a template or master work piece. The attenuation properties of a work piece may be predicted or approximated analytically, e.g., by calculating expected photon transmission such as by using the integral equations for flux above. Attenuation properties may also or alternatively be predicted through simulation, e.g., by ray tracing simulations of x-ray photons through a model of the work piece. Such properties may also or alternatively be determined from images acquired of a similar work piece, such as a master work piece that is known to have the desired dimensions and composition of a batch of work pieces.

In some embodiments of the present invention, patterns in the attenuation properties of an object as the object is rotated may be predicted, if not absolute attenuation properties at a specified projection angle. For example, in one embodiment of the present invention comprising dental CT methods, a human head can be positioned at a predetermined location and angular orientation such that approximate levels of attenuation may be predicted from general anatomy. Additional methods, such as photographing a human subject, e.g., using visible light, or otherwise measuring dimensions of the head of the subject may be utilized to further predict or approximate attenuation characteristics.

In another embodiment of the present invention, attenuation characteristics from different projection angles may be determined by a preliminary scan of the imaging subject, e.g., object or work piece. In one such embodiment, a first scan can be acquired at a relatively high power, which may or may not be the maximum power of the x-ray tube. Power during the first scan may, for example, be at least 5 W, 10 W, 20 W, 50 W, or 100 W, inclusive, or any other integer or non-integer number of watts between or above the enumerated values. Power during the first scan may also, particularly if the source comprises a rotating anode, be at least 1 kW, 5 kW, 10 kW, 50 kW, or 100 kW, inclusive, or any other integer or non-integer number of kilowatts between or above the enumerated values. A subsequent scan or set of scans may revisit or re-expose only those projections that are determined to have noise performance below a predetermined threshold.

In another embodiment of the present invention, a preliminary or scout scan can be taken at 1%, 2%, 3%, 4%, 5%, 10% of the maximum tube power, or any integer or non-integer percentage below or between the enumerated values. In a further embodiment, the beam may alternatively or in addition be collimated to a small region of the object. The beam may, for example, be collimated to 5%, 10%, 15%, 30%, or 25% of the full beam, e.g., of the solid angle of the beam that will be implemented during subsequent scans, inclusive, or any other integer or non-integer percentages between the enumerated values. The scout scan may alternatively be acquired with the tube at full power but moving at a relatively high speed, including but not limited to at least 1 rev/s, 0.75 rev/s, 0.5 rev/s, 0.25 rev/s, 10 rev/hr, 5 rev/hr, or 2 rev/hr, inclusive, or any other speed between or above the enumerated values. The scout scan may also be acquired at 1.5×, 2×, 3×, 4×, 5×, 6×, or any other integer or non-integer factor faster than the average speed to be utilized during subsequent acquisitions. These embodiments of the present invention may be particularly useful in applications wherein limiting radiation dose is desirable, such as when a human patient or living subject is being imaged. Parameters of the scout scan may be tailored such that few to no projections are exposed to enough photons to exceed the desired photon intensity or noise performance of the image.

Determination of target amounts of exposure for each projection angle (S32) may utilize attenuation characteristics information, e.g., as determined in step S31. In one embodiment of the present invention, target exposure times may be determined based on a target noise level for projections in a data set, e.g., a uniform noise level target. In this embodiment, target exposure times may be related to the square root of the transmitted fluence at each projection angle or a similar function of the transmitted fluence at each projection angle. For example, target exposure times may be calculated such that a relationship between the target exposure times $t_i$ and $t_j$ of any two projection angles within a dataset or subset of the dataset is $\sqrt{F_i}/\sqrt{F_j}=t_j/t_i$ where $F_i$ and $F_j$ are transmitted fluence values for the two projection angles.

In one embodiment of the present invention, fluence values that are predicted or evaluated to determine target exposure times, e.g., $F_i$ and $F_j$, can be the mean transmitted fluence over the full detector area. In other embodiments of the present invention, such fluence values can be the minimum fluence value over all beam paths reaching the detector, the minimum fluence value in a predetermined region of the detector, the mean fluence value over a predetermined region of the detector, the mean fluence value over a region of interest in the projection image, or any similar measure or quantification of fluence. In one embodiment, a predetermined region in which fluence is evaluated can be a central region of an image, e.g., a circular, square, rectangular, ellipsoidal, trapezoidal, or any other shaped region comprising up to 20%, 30%, 40%, 50%, 60%, 70%, or 80% of the projection area. A predetermined region in which fluence is evaluated may also be a user-selected or predetermined region of interest (ROI) in the projection images. In one embodiment of the present invention, such an ROI can be selected on a preliminary or previously acquired image before a scan. In another embodiment of the present invention, an ROI can be automatically set using image processing or recognition methods, including but not limited to difference imaging, convolution methods, Fourier transformations, artifact identification, or any other methods. A central region or ROI may be tailored to exclude edges of a projection image that are over-saturated, e.g., as can occur if an object is narrower than the field of view in some projection angles; regions of metal or very highly attenuating features; or other regions of an image that could highly skew mean fluence. Fluence through a predetermined or central region can be predicted or evaluated in any of the methods that have been described, e.g., with respect to step S31, including but not limited to by use of simulations, an image of a master work piece, a scout scan, or similar methods.

One embodiment of the present invention can further comprise acquiring projections in a step-and-shoot mode (S37). In this embodiment, the acquisition hardware or rotary stage may be rotated in angular increments, or steps, between each projection angle once the desired exposure at each projection angle has been achieved. The source and detector may be stationary during each exposure. This embodiment may yield projection images without blurring or resultant image artifacts that can occur when there is relative motion between acquisition hardware and an imaging subject during acquisition.

Other embodiments of the present invention can comprise continuous, e.g., non step-wise, rotation of the imaging hardware or imaging subject during image acquisition. These embodiments may comprise an additional step S33 of calculating a velocity profile, e.g., sequence of velocities or velocity function, that can achieve the target amounts of exposure at each projection angle. The calculated velocity profile can be implemented during acquisition (S34), such as by appropriate acceleration, deceleration, or control of the rotation of imaging hardware or a rotary stage. In these embodiments, the rotation speed may be increased across projection angles exposing relatively x-ray transparent projections and decreased across projection angles exposing relatively x-ray opaque projections. In one embodiment, the exposure times of each projection can be modulated (S35), e.g., such that exposure times may be longer during slowed periods of slowed rotational speeds and shorter during periods of increased rotational speeds. In an alternative embodiment of the present invention, projections may be acquired at a constant rate (S36).

Modulating exposure times, e.g., as in S36, rather than number of exposures, e.g., rather than S35, may incur relatively less noise per projection angle; while electronic dark noise may scale with exposure time, and hence be equal across these embodiments, there can also be an amount of noise associated with the process of reading signals from the detector, which can be incurred each time the detector is read. This detector read noise can be incurred only once per projection image if exposure time is modulated whereas it may be incurred repeatedly if multiple exposures are taken for a given projection image.

In one embodiment of the present invention, variant S34 of FIG. 3 can further comprise grouping adjacent projections with relatively similar attenuation characteristics into subsets. The number of subsets into which a scan can be divided can be relatively small, e.g. less than 10, or may be larger, e.g. up to 500. The number of subsets may further be between 2 and 5, 5 and 10, 10 and 20, 20 and 50, 50 and 100, or 100 and 250, inclusive, or any other number of subsets within or between the enumerated ranges. Target amounts of exposure can be calculated for each subset, e.g., rather than for each projection, such that each projection within a subset is allocated an equal amount of exposure time. This embodiment may reduce the number of rotational speed variations during imaging, or may smooth the velocity profile.

Figure 4:
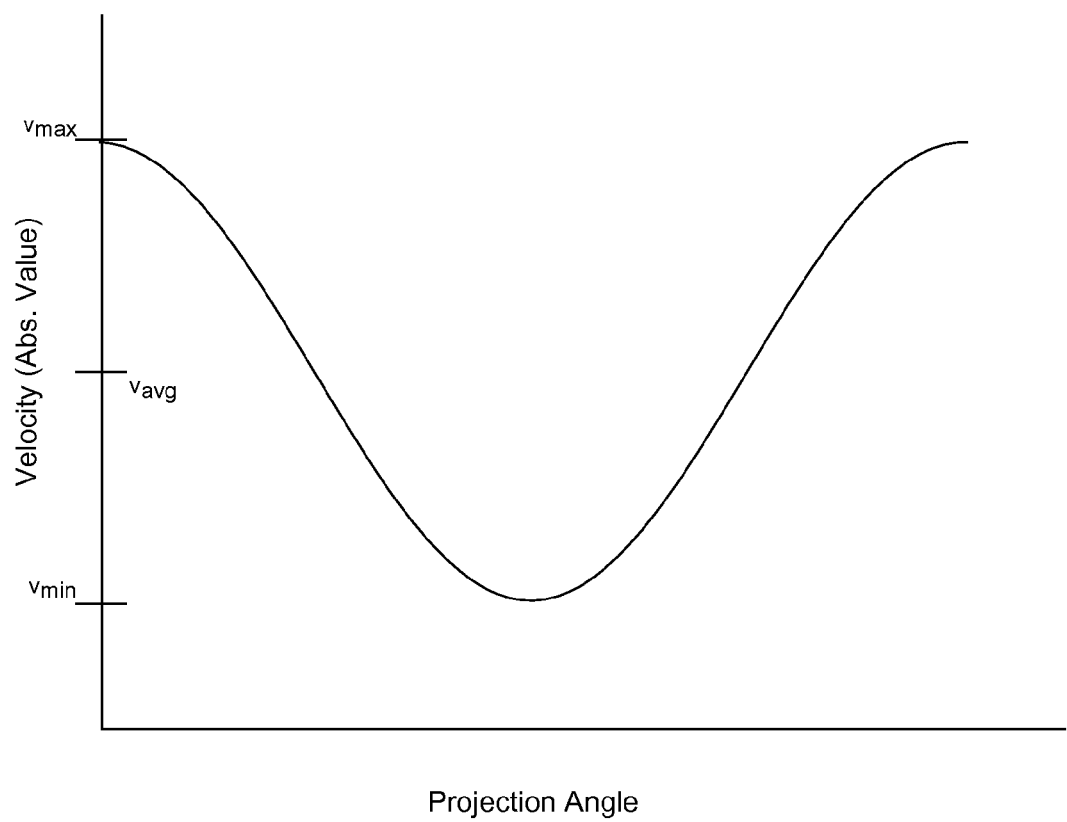
FIG. 4 is a diagram representing one of many possible velocity profiles in embodiments of the present invention.

FIG. 4 is a diagram representing one of many possible velocity profiles in embodiments of the present invention. The velocity profile of FIG. 4 can be sinusoidal, U-shape, quadratic, or otherwise smoothly varying between a maximum velocity $v_{max}$ and a minimum velocity $v_{min}$. Velocity profiles of embodiments of the present invention can share the sinusoidal or smooth characteristics of the profile of FIG. 4 or may have any other shape, e.g., according to the attenuation properties of an imaging subject.

In one embodiment, the velocity profile of FIG. 4 may be tailored for dental CT. The maximum velocity $v_{max}$ may be implemented through projection angles at which photons travel through shortest or least attenuating paths through a head, e.g., through a side profile view of a human head, and the minimum velocity $v_{min}$ may be implemented through the projection angles at which photons travel through the longest or most attenuating paths through a head, e.g. through a head front to back. The horizontal axis in FIG. 4 may represent degrees, radians, or any other unit of angular measure. The plot in FIG. 4 may represent a 180° section of a scan.

The average velocity $v_{avg}$ of a velocity profile in embodiments of the present invention may be any velocity or rotational speed between 1 revolution per second (rev/s) and 0.1 revolutions per hour (rev/hr). The average velocity of embodiments of the present invention for metrology applications may further be between 0.1 and 0.4 rev/hr, 0.4 and 0.7 rev/hr, 0.7 and 1.0 rev/hr, 1.0 and 1.3 rev/hr, 1.3 and 1.6 rev/hr, 1.6 and 2.0 rev/hr, 2.0 and 2.5 rev/hr, 2.5 and 3.0 rev/hr, 3.0 and 3.5 rev/hr, 3.5 and 4.0 rev/hr, 4.0 and 4.5 rev/hr, and 4.5 and 5.0 rev/hr, inclusive, and any other integer or non-integer number of revolutions per hour within or between the enumerated ranges. The average velocity of embodiments of the present invention may further be between 0.1 and 0.2 rev/s, 0.2 and 0.3 rev/s, 0.3 and 0.4 rev/s, 0.4 and 0.5 rev/s, 0.5 and 0.6 rev/s, and 0.6 and 0.7 rev/s, inclusive, and any other integer or non-integer number of revolutions per second within or between the enumerated ranges.

In the embodiment of FIG. 4 and similar embodiments of the present invention, a maximum velocity $v_{max}$ of a calculated velocity profile may be 5×, 4×, 3×, 2×, 1.9×, 1.8×, 1.7×, 1.6×, or 1.5× greater than a non-zero minimum velocity $v_{min}$ inclusive, or any other integer or non-integer factor between or below the enumerated values. For example, $v_{max}$ may be 1.2×, 1.75×, 2.3×, 2.9×, 3.24× $v_{min}$, or greater than $v_{min}$ by any other factor within the enumerated ranges. While tube current modulation techniques can be limited by a maximum tube current available, or by the range over which the tube can be modulated, embodiments of the present invention can be configured to enable a wide range of rotational velocities, e.g., enabling delivery of a particularly wide range in the exposure to different projection angles during a single scan.

Figure 5:
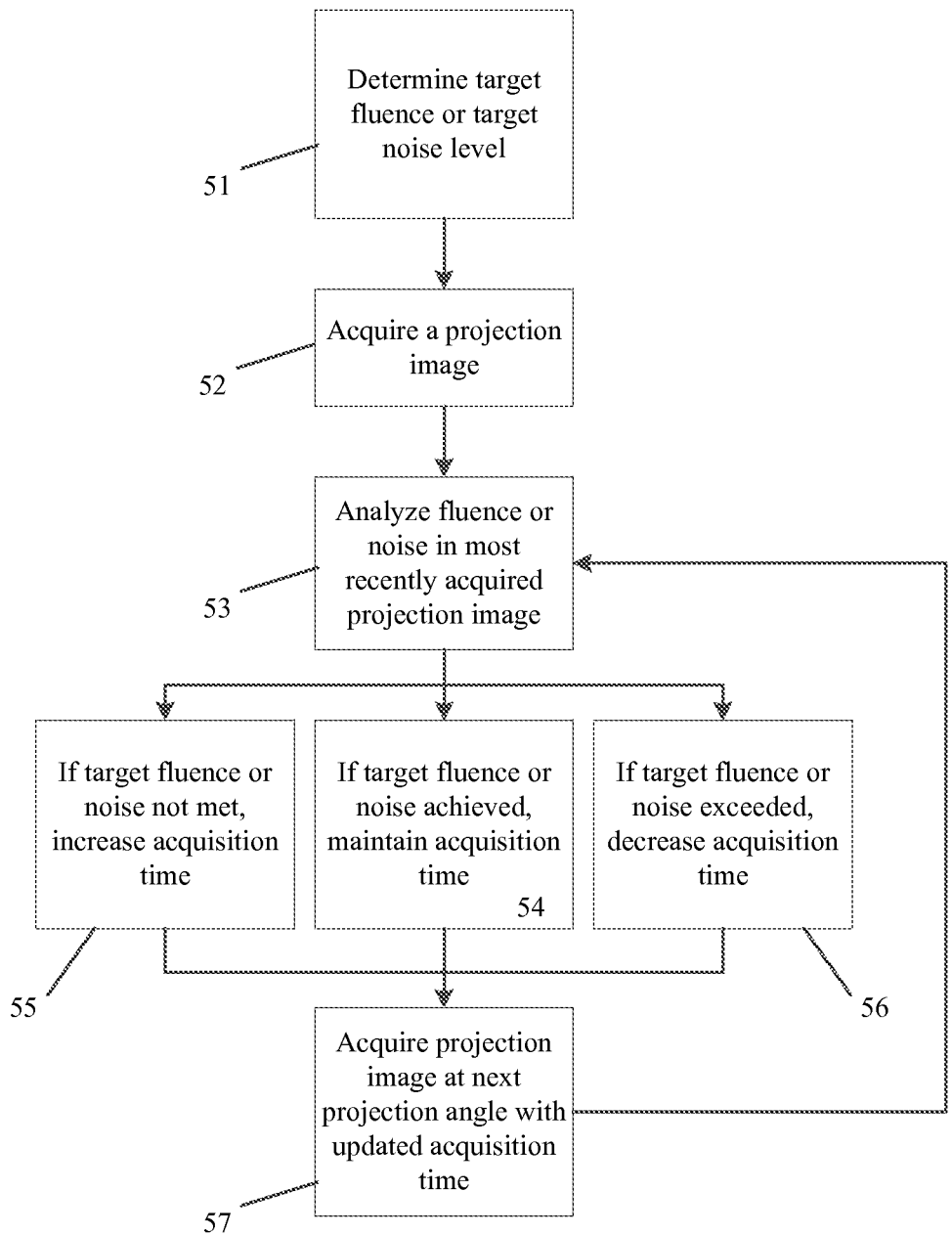
FIG. 5 is a diagram representing an embodiment of the present invention comprising real-time prospective determination of acquisition times achieving targeted levels of fluence at each projection angle.

FIG. 5 is a diagram representing an embodiment of the present invention comprising real-time prospective determination of acquisition times tailored to achieve targeted levels of fluence at each projection angle. In this embodiment, a first step S51 can comprise determining a target amount of fluence or target amount of noise. A first projection image can be acquired with a predetermined acquisition time. In one embodiment, the first projection image may be acquired at an angle expected, e.g., from simulation or prior knowledge, to be one of the least attenuating projections through the imaging subject. The predetermined acquisition time may be any length of time between 0.01 s and 600 s, inclusive. For example, the first projection image may be acquired with an acquisition, e.g., exposure, time of 0.05 s, 0.1 s, 1 s, or 60 s.

The fluence achieved in S52 can be analyzed (S53) after acquisition of the first projection image. An acquisition time for the next projection can be increased (S55), maintained at present level (S54), or decreased (S56) depending on whether fluence in the most recently acquired projection fell below, at, or above the target level of fluence. The next projection image may be acquired with the updated acquisition time, e.g. as shown in step S57. Steps S53 through S57 may be repeated through a full scan of an imaging subject.

The angular difference between contiguous projection images or projection angles in the embodiment of FIG. 5 and other embodiments that have been described may be any angular increment between 0.05° and 2°, inclusive, and any other integer or non-integer increment within the enumerated range. The rotation between projections in this embodiment can, for example, comprise rotation by 0.25°, 0.3°, 0.33°, 0.4°, 0.42°, 0.5°, or 0.6°.

Modification of a subsequent acquisition time, e.g., as in step S55 or S56, can be implemented in a step-and-shoot mode of acquisition by varying the time between steps, e.g., the dwell time at a projection angle. Modification of subsequent acquisition time may also be implemented in other embodiments of the present invention, such as by increasing the velocity of a rotating object or acquisition hardware, e.g., to decrease acquisition time, or decreasing the velocity of a rotating object or acquisition hardware, e.g., to increase acquisition time. An implemented relationship between updated acquisition time and velocity modification can be linear or have any other function. A relationship between target acquisition time and velocity can be determined given the maximum and minimum achievable velocities of the system, acceleration capabilities of the system, total scan time, tube current, and similar parameters.

In step S53, fluence may be analyzed in one or more of a variety of manners. For example, minimum fluence, mean fluence, minimum fluence in a predetermined region, or mean fluence in a predetermined region may be evaluated against a target value. A predetermined region in which fluence is evaluated, e.g., in step S53, may be a central region of an image, e.g., a circular, square, rectangular, ellipsoidal, trapezoidal, or any other shaped region comprising up to 20%, 30%, 40%, 50%, 60%, 70%, or 80% of the projection area. A predetermined region in which fluence is evaluated may also be a user-selectable or predetermined region of interest (ROI) in the projection images. In one embodiment of the present invention, an ROI may be selected by the user on a single or small number of projection images acquired before a scan. In another embodiment of the present invention, an ROI may be automatically set based on a single or small number of projection images based on image processing or recognition methods, including but not limited to difference imaging, convolution methods, Fourier transformations, artifact identification, or any other methods. A central region or ROI may also or alternatively be tailored to exclude any over-saturated regions, e.g., edges, of a projection image, or regions of metal or very highly attenuating features that could highly skew mean fluence.

In some computed tomography applications, image acquisition hardware, e.g., x-ray sources, detectors, or other electronics, can be rotated around the object to be imaged at very high speeds. This type of CT acquisition is of particular utility in the medical field, e.g., for diagnostic or pre- or post-surgical CAT scans. In medical CT, minimizing the total time of the scan may be of high importance, e.g., for time sensitivity of medical procedures or for reducing image artifacts due to patient motion. Many technologies have therefore been developed to rotate acquisition hardware at very high speeds, such that a full scan can be completed in some cases in as little as approximately 300 ms. However, in many other CT applications, time constraints may be lessened. Embodiments of the present invention may be particularly useful for metrology, dental, or other applications wherein total scan time does not need to be kept below 1 s.

Total acquisition time in embodiments of the present invention can vary widely across applications and attenuation properties of imaging subjects. Total acquisition time may be as little as 0.5 s, 1 s, or 5 s, inclusive, and any integer or non-integer number of seconds between or above the enumerated values. Embodiments of the present invention having these relatively low total acquisition times may be particularly useful for dental CT, small-scale metrology, or similar applications. Total acquisition times may also be as long as 0.5 h, 1 h, 2 h, or 3 h, inclusive, or any integer or non-integer number of hours between or below the enumerated values. Systems with relatively long total acquisition times may be particularly useful for large-scale or high-resolution metrology or similar applications. Computed tomography-based coordinate measurement methods can provide accurate validation or evaluation of irregularities for industrial metrology applications. Relatively long total scan times can be acceptable in industrial metrology, as high image quality can be important for precise coordinate measurement and validation, and work pieces may be highly attenuating.

Dental CT is also a growing field for computed tomography and may have lessened time constraints relative to medical CT since a dental patient can be positioned in a manner less prone to voluntary or involuntary movement. The patient may, for example, be provided with a given structure for the duration of a scan to ensure accurate and still positioning. Involuntary motions, e.g., cardiac motion or other organ motion, are also relatively absent from dental imaging. Other applications may exist wherein a living subject can be imaged with CT under lessened time constraints.

Embodiments of the present invention can be implemented within cone beam, fan beam, point source, or any other CT frameworks. Embodiments of the present invention may be particularly useful for cone beam systems as these systems may utilize flat panel detectors. Cone beam CT systems may also operate at longer scan times or slower acquisition rates than other CT frameworks.

Embodiments of the present invention may also be implemented within other applications, including but not limited to tomosynthesis applications, such as digital tomosynthesis or tomosynthesis for mammography. In these applications, projection images can be acquired through a set of angles comprising less than 180 degrees around the subject. Images can, for example, be acquired through an angular set comprising between 5 degrees and 60 degrees, 10 degrees and 55 degrees, 15 degrees and 50 degrees, or 20 degrees and 45 degrees, inclusive, or any other integer or non-integer number of degrees within or between the enumerated ranges. A number of projections acquired over this angular set can be relatively less than in computed tomography procedures; for example, a set of projection images can comprise between 3 and 30 projections, 5 and 25 projections, 7 and 20 projections, or 9 and 15 projections images can be acquired, inclusive, or any other number of images. Exposure times for projections in this set can be controlled according to any of the embodiments of the present invention that have been described.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A method of acquiring an X-ray image of an object comprising:
    positioning said object in field of view of an X-ray image acquisition device;
    selecting a set of a plurality of unique projection angles between said X-ray image acquisition device and an axis through said object, wherein said set spans at least 45 degrees around said object;
    selecting a targeted X-ray exposure at a detector region for each of said projection angles;
    determining a targeted total exposure duration time for each of said projection angles corresponding to said targeted X-ray exposure;
    implementing said plurality of targeted total exposure duration times in said X-ray image acquisition device over said set of projection angles to acquire an image data set; and
    reconstructing an X-ray image from said image data set.

2. The method of claim 1 further comprising:
    increasing said targeted exposure duration time with at least one of said projection angles based on increase of attenuation at said projection angle.

3. The method of claim 1 further comprising:
    reducing saturation of said detector by reducing said targeted exposure duration time with at least one of said projection angles.

4. The method of claim 1 further comprising:
    adjusting said targeted exposure duration time based on attenuation characteristics information.

5. The method of claim 1 further comprising:
determining attenuation characteristics at each of said projection angles.

6. The method of claim 1 further comprising:
controlling total exposure duration times by modulating individual exposure time of each exposure.

7. The method of claim 1 further comprising:
predicting attenuation characteristics at each of said projection angles.

8. The method of claim 1 further comprising:
evaluating said targeted X-ray exposure at a user-selected region of interest.

9. The method of claim 1 further comprising:
evaluating said targeted X-ray exposure at a predetermined region of interest.

10. The method of claim 1 further comprising:
excluding edges of a projection image that are over-saturated.

11. The method of claim 1 further comprising:
adjusting said targeted total exposure duration times at said projection angles depending on fluence in a previously acquired projection.

12. The method of claim 1 wherein said region is a full detector area.

* * * * *